United States Patent [19]

Drury et al.

[11] Patent Number: 4,614,816
[45] Date of Patent: Sep. 30, 1986

[54] PREPARATION OF CARBOXYLIC ACIDS AND ESTERS THEREOF

[75] Inventors: David J. Drury, Twickenham; Peter S. Williams, Hull, both of England

[73] Assignee: BP Chemicals Limited, London, England

[21] Appl. No.: 541,379

[22] Filed: Oct. 13, 1983

[30] Foreign Application Priority Data

Oct. 20, 1982 [GB] United Kingdom ............... 8229988
Jan. 13, 1983 [GB] United Kingdom ............... 8300888

[51] Int. Cl.$^4$ ..................... C07C 67/38; C07C 51/353
[52] U.S. Cl. ............................. 560/243; 260/410.9 R; 260/413; 560/1; 560/105; 560/121; 560/123; 560/124; 560/174; 560/177; 562/400; 562/496; 562/504; 562/505; 562/506; 562/577; 562/606
[58] Field of Search ................... 560/243, 233, 1, 105, 560/121, 123, 124, 174, 177; 562/522, 606, 400, 496, 504, 505, 506, 577; 260/410.9 A, 413 AC

[56] References Cited

U.S. PATENT DOCUMENTS 2,013,338  9/1935  Carpenter ........................... 562/606
3,816,489  6/1974  Craddock ........................... 260/413
3,849,456  11/1974  McMullen ..................... 260/410.9 R
4,414,409  11/1983  Waller ................................. 562/522

FOREIGN PATENT DOCUMENTS 92350 10/1983 European Pat. Off. .
1484367  6/1967 France .
56-133242 10/1981 Japan .

OTHER PUBLICATIONS

Kolomnikov, Kinetics and Catalysis, 13, p. 227 (1972).
Kolomnikov, Tetrahedron Letters, 46, p. 4435 (1971).

Primary Examiner—Michael L. Shippen
Attorney, Agent, or Firm—Brooks, Haidt, Haffner & Delahunty

[57] ABSTRACT

A carboxylic acid or an ester thereof having at least two carbon atoms more than formic acid is prepared by reacting at elevated temperature e.g. 100° to 250° C. formic acid or a formate ester with an olefin e.g. ethylene in the presence of, as catalyst, a Group VIII noble metal e.g. iridium, preferably promoted by iodide, to cause addition of the formic acid or ester to the olefin and form the a higher acid e.g. propionic acid or ester thereof.

A strong acid such as a sulphonic acid may be used as a copromoter. The catalyst is employed in solution.

13 Claims, No Drawings

PREPARATION OF CARBOXYLIC ACIDS AND ESTERS THEREOF

This invention relates to a process for the prepartion of carboxylic acids or esters thereof by the reaction of formic acid or an ester thereof with an olefin in which the formic acid or formate ester is added to the olefin to form a higher carboxylic acid or an ester thereof.

The addition of a formate ester to an olefin has been previously described in U.S. Pat. No. 3,849,456 in which the reaction is catalysed by a peroxide. The reaction is relatively unselective in that it yields a broad mixture of carboxylic acid esters.

It has now been found that the addition of formic acid or an ester thereof to an olefin can be catalysed by a noble Group VIII metal such as iridium which has the advantage that it yields a narrower mixture of carboxylic acid esters than the above mentioned peroxide catalysed reaction. Moreover, by appropriate adjustment of the reaction conditions it can be made highly selective in that for example the higher carboxylic acid and its ester product can exceed 90% by weight of the liquid phase product.

Thus, according to the present invention a process for the preparation of a carboxylic acid or ester thereof having at least two carbon atoms more than formic acid comprises reacting at elevated temperature formic acid or an ester thereof with an olefin in the presence of, as catalyst, an effective amount of a Group VIII noble metal to cause addition of the formic acid or ester to the olefin and form the acid or ester having at least two carbon atoms more than formic acid.

Conveniently the Group VIII noble metal is a compound which is preferably soluble in the reactants and products under the reaction conditions.

By Group VIII noble metal we mean ruthenium, rhodium, palladium, osmium, iridium and platinum.

Preferably the Group VIII metal compound is an iridium compound for example a salt or complex such as $[Ir(cyclooctadiene)Cl]_2$, $Na_2IrCl_6 \cdot XH_2O$, $HIrCO[P(C_6H_5)_3]_3$, $ClIrCO(PEt_3)_2$, $IrCl_3 \cdot XH_2O$, $IrI_3 \cdot XH_2O$, $Na_3Ir(NO_2)_6 \cdot XH_2O$, $[(C_5H_5)_2Ir]NO_3$, $Ir_4(CO)_{12}$, $IrH_3[P(C_6H_5)_3]_3$, and $(C_8H_{12})_2IrSnCl_3$. Preferred compounds are $[Ir(cyclooctadiene)Cl]_2$, $IrCl_3 \cdot XH_2O$, $IrBr_3 \cdot XH_2O$, $IrI_3 \cdot XH_2O$. and iridium trisacetylacetonate. The symbol X indicates differing degrees of hydration and varies from 0 to 12. Metallic iridium can be employed.

Preferably a halide promoter such as an iodide promoter is also present with the Group VIII noble metal.

Suitable iodides are alkyl iodides particularly lower alkyl iodides such as methyl iodide. Suitable amounts of iodide in relation to the Group VIII noble metal are from 1 to 500 moles for each mole of Group VIII noble metals.

When formic acid is a reactant, some of the iodide tends to be converted to a carboxylic acid by reaction with the formic acid. For example methyl iodide is converted to acetic acid. It is therefore preferred that the alkyl group of the iodide promoter is the same as that in the acid being formed as the reaction product. Thus it is preferred to use ethyl iodide when producing propionic acid.

The reaction can be effected in either the gaseous or liquid phase. In the latter a solvent for the liquid reactants is conveniently employed. Suitable solvents are carboxylic acids of formula $RCO_2H$ where R is $C_1$ to $C_8$ aliphatic, $C_4$ to $C_8$ cycloaliphatic, $C_7$ to $C_{12}$ aralkyl or $C_6$ to $C_{10}$ aryl.

Preferably a strong acid which is compatible with the catalyst is also present as a copromoter for the catalyst. By compatible is meant that the strong acid should not deactivate the catalyst. When the acid is present the iodide promoter can be omitted. By strong acid is meant one which is significantly more acidic than the carboxylic acid employed as the solvent, for example an acid having a pK of less than 0 (as measured in water). Suitable strong acids are mineral acids and sulphonic acids such as p-toluene sulphonic acid and methane sulphonic acid employed in an amount, for example, of between 1.5 and 5.0% by wt. The concentration of acid may vary widely. Usually concentrations up to 10% by wt are convenient, but a liquid sulphonic acid can for example be employed.

Suitable olefins for use in the present invention are those having from 2 to 30 carbon atoms of formula:

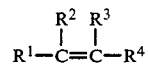

in aliphatic heteroaliphatic, acyclic or cycloaliphatic form wherein $R^1$, $R^2$, $R^3$ and $R^4$ are independently either hydrogen, halogen, alkyl, alkenyl, aryl, cycloalkyl or cycloalkenyl moieties or, in a heteroaliphatic compound, are moieties containing nitrogen, phosphorus, sulphur, halogen or oxygen atoms or, in a cycloaliphatic compound $R^2$ and $R^3$ are linked. Suitable compounds having the above formula include ethylene; propylene; butene-1; butene-2; pentenes; hexenes; octenes; hexadecene; 2-methylpropene; styrene; 1,4-hexadiene; acrolein; methyl vinyl ketone and 2-cyclohexylbutene. If desired, mixtures of the aforesaid olefins may be employed.

Suitable esters of formic acid are those of formula $HCO_2R$ where R is a $C_1$ to $C_8$ aliphatic group.

Conveniently the reaction is carried out at a temperature in the range from 100° to 250° C., preferably from 170° to 215° C.

In the case of a gaseous olefin the pressure is desirably at least 10 psi in excess of autogeneous pressure. Convenient pressures are in the range 200 to 1200 psi.

In order to reduce undesirable decomposition of formic acid the concentration of formic acid is preferably maintained low, for example 25% by wt of the reaction solution and the partial pressure of olefin high, for example in the case of ethylene greater than 300 psi. In reactions involving formate esters such as methyl formate, similar conditions serve to reduce loss of selectivity due to isomerisation of the methyl formate to acetic acid which is known to be catalysed under certain conditions by iodide promoted iridium.

Preferably the reaction is effected in the substantial absence of oxygen, although carbon monoxide or inert gases such as nitrogen or hydrogen can be present.

The products of the present invention have a wide variety of uses, for example, propionic acid is employed in agriculture as a preservative.

The invention is illustrated by the following Examples.

EXAMPLE 1

Reaction of methyl formate with ethylene

In the examples all the reactants and products except the ethylene in Examples 1 to 5 and 7 to 11 were added in the liquid phase, and the catalysts were employed in solution.

The pressures reached inside the reactors were not measured in every case.

A corrosion resistant autoclave of 100 ml capacity equipped with rotary stirrer was charged with a reaction mixture comprising 15.2 g methyl formate, 8.1 g methyl iodide as promoter, 40.5 g acetic acid as solvent and 0.1 g $IrCl_3$. The autoclave was closed, flushed three times with ethylene, and pressurised whilst stirring with 400 psi ethylene. The autoclave was then heated and the temperature maintained at 200° C. for 2.5 hours. After cooling and depressurisation, the product was recovered and analysed by gas liquid chromatography (G.L.C.). It was found to contain by weight 13.5% propionic acid, 2.5% methyl propionate, 22.8% methyl acetate (formed by transesterification), and 6.3% unreacted methyl formate.

EXAMPLE 2

Reaction of methyl formate with ethylene

In this example propionic acid was employed as solvent in order to determine the amount of acetic acid formed under the conditions of Example 1.

To the autoclave of Example 1 was charged 15.0 g methyl formate, 9.0 g methyl iodide as promoter, 40.5 g propionic acid as solvent, and 0.1 g $IrCl_3$. The procedure of Example 1 was then followed. Analysis of the product showed it to contain only 0.8% acetic acid, trace quantities of methyl acetate, and 8.3% unreacted methyl formate.

Propionate was also formed but the amount produced could not be measured accurately because of the propionic acid solvent used.

This example demonstrates that under the conditions of Example 1 only small quantities of acetic acid are formed.

Comparison of Examples 1 and 2 shows that 95% of the liquid phase reaction product is propionate (i.e. propionic acid and ester).

EXAMPLE 3

Reaction of methyl formate with ethylene using a strong acid as copromoter.

A 500 ml corrosion resistant autoclave equipped with a rotary stirring system was charged with a reaction mixture comprising the following: methyl formate 120 g, acetic acid 102 g as solvent, methyl iodide 48 g as promoter, iridium trichloride 0.4 g, and p-toluene sulphonic acid 12 g as copromoter. The autoclave was sealed, flushed three times with ethylene, and was then pressurised, whilst stirring, with 400 psi ethylene. The autoclave was then heated to 200° C., and held at this temperature for 30 minutes. After cooling and depressurising, the product was recovered and analysed by G.L.C. It contained by weight 10% propionic acid, 12.7% methyl propionate, 24.9% methyl acetate and 10.5% unreacted methyl formate.

EXAMPLE 4

Reaction of methyl formate with ethylene.

Example 3 was repeated, except with the p-toluene sulphonic acid copromoter absent. The product was found to contain only 4.0% propionic acid and 1.4% methyl propionate, together with 18.7% methyl acetate and 24.3% unreacted methyl formate.

Comparison of Examples 3 and 4 show that the a higher yield of propionic acid and its ester are obtained when the strong acid is included in the reaction mixture.

EXAMPLE 5

Reaction of methyl formate with ethylene

The autoclave of Example 1 was charged with 30.0 g methyl formate, 25.0 g acetic acid as solvent, 12.6 g methyl iodide as promoter, 3.0 g p-toluene sulphonic acid as copromoter and 0.1 g ruthenium trichloride. The autoclave was flushed three times with ethylene, sealed, and pressurised whilst stirring with 400 psi ethylene. The reactor was heated to 200° C. for 3 hours, cooled, and the contents removed. Analysis by G.L.C. showed the product to contain 0.65% wt methyl propionate and 0.4% wt propionic acid.

EXAMPLE 6

Reaction of methyl formate with hexene-1

The autoclave of Example 3 was charged with 60.0 g hex-1-ene, 60.0 g methyl formate, 120.0 g propionic acid as solvent, 47.9 g methyl iodide as promoter, 12.0 g p-toluene sulphonic acid as copromoter, and 0.395 g iridium trichloride. The autoclave was flushed three times with nitrogen, sealed, and heated to 200° C. After 6 hours at this temperature the reactor was cooled, and the product analysed by G.L.C. It was found to contain by weight 4.5% methyl heptanoate and 6.5% heptanoic acid.

EXAMPLE 7

Reaction of formic acid with ethylene

A 500 ml corrosion-resistant autoclave was charged with 50.9 g formic acid solution (90% by weight in water), 29.8 g methyl iodide as promoter, 0.417 g iridium trichloride and 150.7 g acetic acid as solvent. The autoclave was sealed, flushed three times with ethylene, and then pressurised with 650 psi ethylene whilst stirring. The reactor was heated to 200° C. and held at this temperature for 1½ hours before cooling. Gas liquid chromatography (GLC) analysis showed the product to contain, by weight, 12.6% propionic acid.

EXAMPLE 8

Reaction of formic acid with ethylene

The autoclave of Example 7 was charged with 50.0 g formic acid solution (90% by weight in water), 29.5 ethyl iodide as promoter, 0.404 g iridium trichloride, 149.8 g acetic acid as solvent and 12.3 g methane sulphonic acid as copromoter. The autoclave was flushed three times with ethylene, sealed, and pressurised with 600 psi ethylene whilst stirring. The reactor was heated, and held at 200° C. for 30 minutes before cooling. GLC analysis of the product showed it to contain, by weight, 22.4% propionic acid.

In this example the alkyl group of the copromoter was the same as that in the propionic acid product.

EXAMPLE 9

Reaction of formic acid with ethylene in the absence of carboxylic acid solvent

A 100 ml corrosion resistant autoclave was charged with 40.5 g formic acid solution (90% by weight in water), 7.6 g methyl iodide as promoter and 0.103 g iridium trichloride. The autoclave was sealed, flushed three times with ethylene and pressurised with 400 psi ethylene whilst stirring. The reactor was heated and held at 200° C. for 1½ hours before cooling. GLC analysis of the product was carried out, and showed it to contain 20.9% by weight of propionic acid.

EXAMPLE 10

Reaction of methyl formate with ethylene in the absence of a carboxylic acid solvent.

The autoclave of example 1 was charged with 35.0 g methyl formate, 5.6 g methyl iodide as promoter, 4.0 g p-toluene sulphonic acid as copromoter, and 0.1 g iridium trichloride. The autoclave was flushed several times with ethylene, pressurised with 400 psia ethylene, sealed, and heated at 200° C. for 1 hour. During this period the pressure did not rise above 700 psia. The autoclave was then cooled, and the product recovered and analysed by GLC. It was found to contain by weight 17.8% methyl propionate, 7.8% methyl acetate, 1.5% propionic acid, and 1.1% acetic acid.

This example together with Examples 11 and 12 below demonstrate that a carboxylic acid solvent is not required when a strong acid is employed.

EXAMPLE 11

Reaction of methyl formate with ethylene

The autoclave of example 1 was charged with 35.0 g methyl formate, 5.5 g methyl iodideas promoter, 4.0 g methane sulphonic acid as copromoter, and 0.139 g iridium trisacetylacetonate. The procedure of example 10 was then followed, except that the reaction time at 200° C. was ½ hour. The product was found to contain by weight 21.6% methyl propionate, 7.8% propionic acid, 11.8% methyl acetate and 5.0% acetic acid.

EXAMPLE 12

Reaction of methyl formate with hex-1-ene in the absence of solvent

The autoclave of example 1 was charged with 15.0 g methyl formate, 25.0 hex-1-ene, 5.0 g methyl iodide as promoter, 4.0 g methane sulphonic acid as copromoter, and 0.106 g iridium trichloride. The autoclave was then flushed several times with nitrogen and pressurised with 300 psia nitrogen. The reaction mixture was then heated to 200° C. and this temperature maintained for 3 hours; during which time the pressure did not exceed 650 psi. The autoclave was then cooled and the product analysed by GLC. It was found to contain by weight ca. 26% methyl n-heptanoate, ca. 10% methyl i-heptanoate, ca. 3.5% hexyl heptanoate (and isomers), ca. 8% n-heptanoic acid and ca. 3% i-heptanoic acid.

We claim:

1. A process for the preparation of a carboxylic acid or an ester thereof, the carboxylic acid having at least two carbon atoms more than formic acid, which comprises reacting, at elevated temperature, formic acid, or an ester thereof, with an olefin in the presence of, an effective amount of
   a catalyst comprising (a) iridium and (b) a strong acid having a pK of less than 0 (as measured in water) wherein the catalyst causes the addition of the formic acid or ester to the olefin thereby forming the acid having at least two carbon atoms more than formic acid or the ester thereof.

2. A process as claimed in claim 1 wherein a halide promoter is present with the Group VIII noble metal.

3. A process as claimed in claim 2 wherein the halide promoter is an alkyl iodide.

4. A process as claimed in claim 3, wherein the acid having at least 2 carbon atoms more than formic acid is of formula $RCO_2H$ and the halide promoter is of formula RX where X is halide and the R groups of the acid and halide are identical, and
   wherein R is alkyl.

5. A process as claimed in claim 1 wherein the strong acid is a sulphonic acid.

6. A process as claimed in claim 5, wherein the strong acid is p-toluene sulphonic acid or methane sulphonic acid.

7. A process as claimed in claim 1 wherein the reaction is carried out at a temperature in the range 100° to 250° C. and at a pressure in the range 200 to 1200 psi.

8. A process as claimed in claim 1 wherein the process is operated in the liquid phase and a solvent for the liquid reactants and products is employed.

9. A process as claimed in claim 8 wherein the solvent is a carboxylic acid.

10. A process as claimed in claim 9, wherein the carboxylic acid solvent is of the formula $RCO_2H$, where R is $C_1$ to $C_8$ aliphatic, $C_4$ to $C_8$ cycloaliphatic, $C_7$ to $C_{12}$ aralkyl or $C_6$ to $C_{10}$ aryl.

11. A process as claimed in claim 1, wherein the olefin is selected form the group consisting of ethylene; propylene; butene-1; butene-2; pentenes; hexenes; octenes; hexadecene; 2-methyl-propene; styrene; 1,2-hexandiene; acrolein; methyl vinyl ketone; 2-cyclohexylbutene, and the mixtures of the aforesaid olefins.

12. A process as claimed in claim 11, wherein the olefin is ethylene or hexene-1.

13. A process as claimed in claim 12, wherein the olefin is ethylene.

* * * * *